(12) United States Patent
Bedell

(10) Patent No.: US 7,273,468 B2
(45) Date of Patent: Sep. 25, 2007

(54) STEERABLE FIBEROPTIC EPIDURAL BALLOON CATHETER AND SCOPE

(75) Inventor: Raymond L. Bedell, 95 W. Golf Course Dr. Suite 103, Logan, UT (US) 84123

(73) Assignee: Raymond L. Bedell, Logan, UT (US)

( * ) Notice: Subject to any disclaimer, the term of this patent is extended or adjusted under 35 U.S.C. 154(b) by 140 days.

(21) Appl. No.: 10/169,641

(22) PCT Filed: Jan. 5, 2001

(86) PCT No.: PCT/US01/00405

§ 371 (c)(1),
(2), (4) Date: Jul. 3, 2002

(87) PCT Pub. No.: WO01/49356

PCT Pub. Date: Jul. 12, 2001

(65) Prior Publication Data

US 2003/0004460 A1 Jan. 2, 2003

Related U.S. Application Data

(60) Provisional application No. 60/174,771, filed on Jan. 6, 2000.

(51) Int. Cl.
A61M 31/00 (2006.01)
A61M 37/00 (2006.01)
A61M 29/00 (2006.01)
A61M 25/00 (2006.01)
A61B 1/06 (2006.01)

(52) U.S. Cl. .............. 604/95.04; 604/96.01; 604/264; 604/528; 604/509; 604/510; 600/114; 600/115; 600/160

(58) Field of Classification Search ............. 604/95.04, 604/96.01, 97.01–99.03, 164.13, 264, 523, 604/528, 510; 600/434, 585, 114, 115, 146–150, 600/160–183; 606/15, 16
See application file for complete search history.

(56) References Cited

U.S. PATENT DOCUMENTS

| | | | |
|---|---|---|---|
| 4,519,403 A | | 5/1985 | Dickhudt |
| 4,947,827 A | * | 8/1990 | Opie et al. .................. 600/108 |
| 4,961,738 A | * | 10/1990 | Mackin ....................... 606/15 |
| 4,976,710 A | * | 12/1990 | Mackin ....................... 606/15 |
| 5,084,016 A | | 1/1992 | Freeman et al. |
| 5,090,959 A | * | 2/1992 | Samson et al. ............. 600/116 |
| 5,195,541 A | | 3/1993 | Obenchain |
| 5,215,105 A | * | 6/1993 | Kizelshteyn et al. ........ 128/898 |
| 5,232,442 A | | 8/1993 | Johnson et al. |
| 5,336,182 A | * | 8/1994 | Lundquist et al. .......... 604/528 |
| 5,372,587 A | * | 12/1994 | Hammerslag et al. ... 604/95.04 |
| 5,399,164 A | * | 3/1995 | Snoke et al. ............. 604/95.04 |
| 5,690,669 A | * | 11/1997 | Sauer et al. ................. 606/196 |
| 5,740,808 A | * | 4/1998 | Panescu et al. ............. 600/424 |

(Continued)

Primary Examiner—Catherine S. Williams
(74) Attorney, Agent, or Firm—Steven L. Nichols; Rader, Fishman & Grauer PLLC

(57) ABSTRACT

Devices for and methods of treating afflictions occurring in a body cavity, such as the epidural space. The methods and devices provide for fluoroscopic assisted placement of a fiber optic catheter/scope with a balloon tip. These devices and methods would perform decompression surgery, neuroplasty, and mechanical lysis of adhesions (and other afflictions), as well as allowing small operating and therapeutic instruments under direct visualization.

22 Claims, 7 Drawing Sheets

U.S. PATENT DOCUMENTS 5,857,996 A    1/1999  Snoke
5,904,648 A *  5/1999  Arndt et al. ................ 600/120

6,030,360 A *  2/2000  Biggs ...................... 604/95.01

* cited by examiner

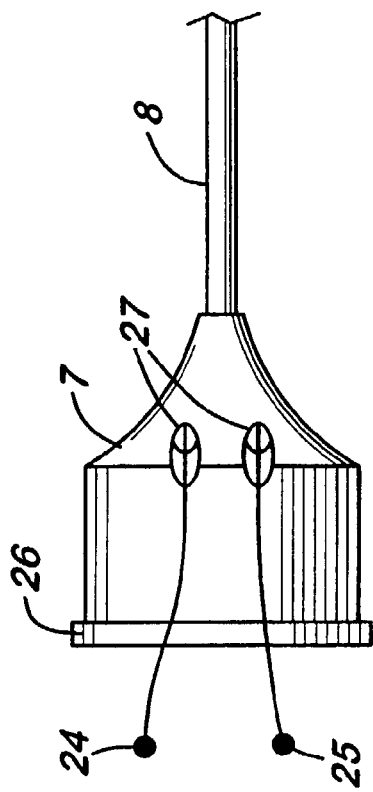
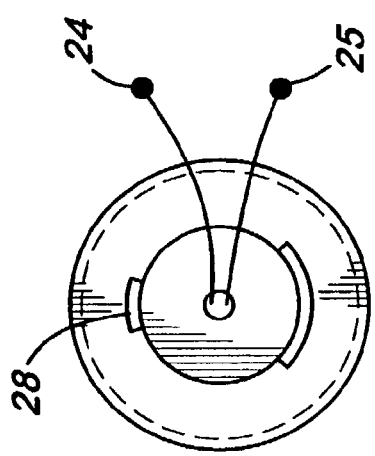
FIG. 5B
FIG. 5A
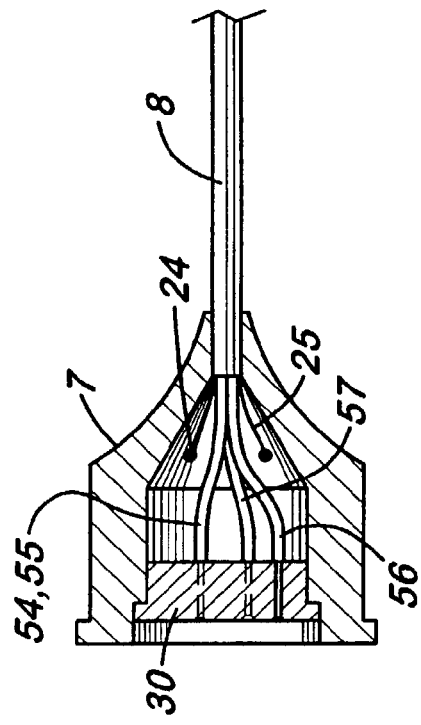
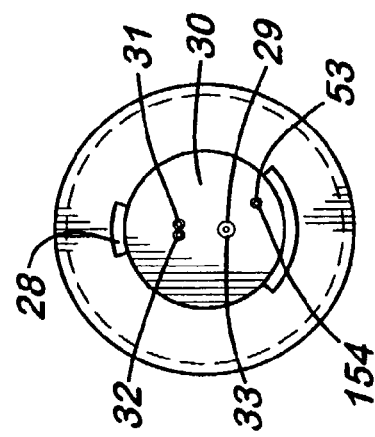
FIG. 6B
FIG. 6A

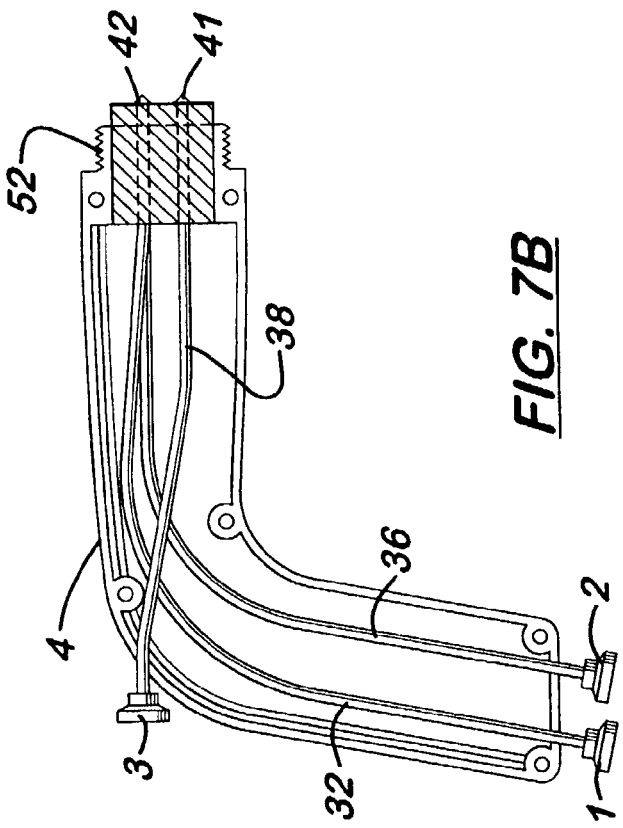
FIG. 7E
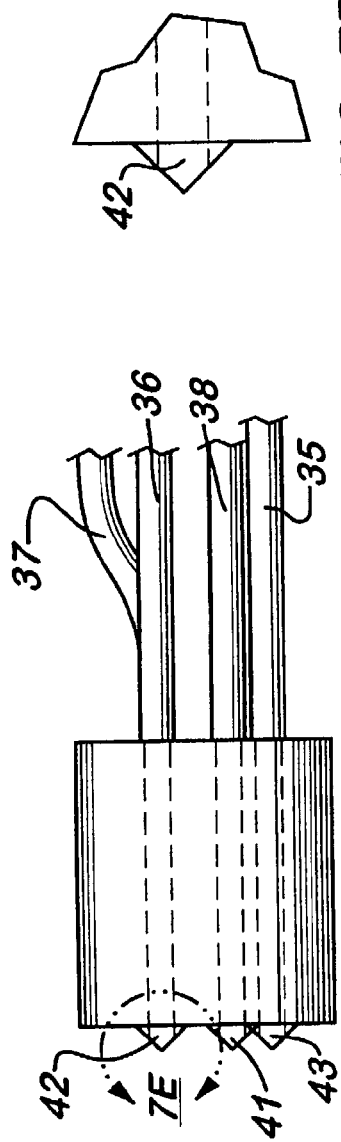
FIG. 7B
FIG. 7D
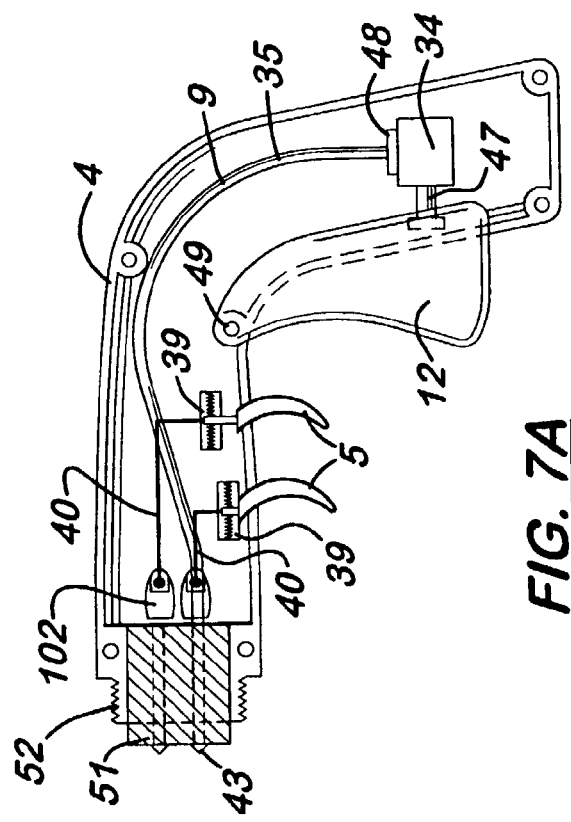
FIG. 7C
FIG. 7A

STEERABLE FIBEROPTIC EPIDURAL BALLOON CATHETER AND SCOPE

REFERENCES TO RELATED APPLICATIONS

This application claims priority from U.S. Provisional Patent Application No. 60/174,771, filed Jan. 6, 2000 and PCT application No. PCT/US01/00405, the disclosures of which are incorporated herein by reference.

FIELD OF THE INVENTION

The present invention generally relates to medical devices and methods for using the same. In particular, the present invention relates to a method for treating fibrotic lesions in the epidural space of the spinal column and to a device for facilitating such a method. Specifically, the present invention relates to steerable fiberoptic catheter/scope with a balloon tip that is to be used in and around the epidural space (and other body cavities) to dilate the epidural space, decompress adhesions, and remove scar tissue.

BACKGROUND OF THE INVENTION

Back pain, and particularly lower back pain, is a common disabling problem of the body. In the back or posterior end of the body, the epidural space is located in and extending the length of the spine. The epidural space contains fat, connective tissue, blood vessels, lymphatic vessels, nerve fibers, as well as other structures. FIGS. 9a and 9b illustrate, the crescent shaped cross-section of the epidural space 110 and its position within the spinal column 118. The epidural space 110 is defined along the edge (or side) by dura mater 112 that surrounds spinal cord 118. The epidural space is further defined along a second edge (or side) by the periosteum of the bony vertebrae or by ligamentum-flavum 114 at the vertebral interspaces. Along the interior surface of the periosteum or ligamentum-flavum 114 lies venus plexis 119, a complex configuration of veins. Web-like fibrosis 120 may adhere to dura mater 112 and the periosteum and/or the ligamentum-flavum 114. These fibrosis may be formed in a random manner or in layers that form lesions extending across epidural space 110 or parallel thereto.

The various lesions, as well as cystical masses and nerve damage, which occur in and around the epidural space can cause various back problems for the human body. Fibrosis often comprise an epidural lesion, which may have a consistency ranging from very soft to tougher, scar-tissue.

An epidural lesion may extend through the epidural space over the length of two or three vertebrae and are believed to be a source of lower back pain and possibly sciatica in human beings. These lesions are believed to be caused by postoperative scarring of nerves, particularly from laminectomy procedures. A ruptured disc or a leaking disc, caused by an annular tear, also are believed to be a cause. Adhesions are often attached to the nerve roots or sleeves themselves causing compression and/or tethering of these neural elements, causing intractable pain and disability. This condition is often related to post surgical changes related to inflammation or bleeding in the epidural spaces resulting in scar tissue formation with resultant contraction over time. Many other conditions can contribute to the above affliction in the epidural space, including leakage of material from the compromised inter-vertebral disc, infection, tumor, and a number of other medical conditions. The result of these afflictions is loss of the epidural space and/or inflammation in the same space. These lesions generally have their greatest negative effect when they exist in the anterior lateral epidural space.

Epidural lesions and other epidural afflictions have been treated by numerous methods. One known method is surgical exploration. Unfortunately, surgical exploration is difficult, time-consuming and often results in a painful postoperative recovery.

Epidural afflictions have also been investigated and treated through the methods and devices disclosed in U.S. Pat. No. 5,232,442, the disclosure of which is incorporated herein by reference. Epidural lesions also have been treated by fluid lysis. In fluid lysis, an epidural catheter often comprising a flexible tubular shaft having an open distal end is introduced between the vertebrae of the spinal column and into the epidural space. The distal end of the epidural catheter is positioned adjacent the fibrosis comprising the lesion. A desired volume of fluid is then delivered through the catheter and directed against the fibrosis with enough force to break the web-like layers comprising the lesion. Unfortunately, fluid lysis can be ineffective because the fluid takes the path of least resistance upon leaving the distal end of the catheter and fails to impact the fibrosis with enough force to destroy the lesion. Consequently the lesion is not removed and the procedure must be repeated.

Fluoroscopic observation techniques have also been used to investigate and treat various sources of problems associated with back pain. See, for example, U.S. Pat. No. 5,215,105, the disclosure of which is incorporated herein by reference. These fluoroscopic techniques help guide devices, but fail to give a detailed picture of structures within vessels or cavities, such as the epidural space, and therefore are limited in their ability to identify the source of back pain. For example, fiber optic scopes (or fiberscopes) have been used for various types of surgery. These fiberscopes often are inserted into a vein or an artery for viewing blockage or the like within the vein or artery. The epidural space, however, has not fully been explored using visual techniques because the epidural space, as described above, does not take the form of a vein or artery. Instead, the epidural space collapses around an instrument or device inserted therein.

Endoscopes have been used to investigate and treat internal areas or organs within a body vessel or cavity, such as the epidural space. An elongated insertable part of the endoscope is inserted through a tube or sleeve that is itself inserted into a body vessel or cavity, or directly into the body vessel or cavity itself. See, for example, U.S. Pat. No. 5,195,541, the disclosure of which is incorporated herein by reference. These endoscopes, however, are relatively large with respect to a catheter and, therefore, difficult and dangerous to operate.

Practitioners have also used contrast injections under fluoroscopy to investigate and treat epidural afflictions. More recently, epidurography and/or epiduroscopy has improved diagnosis and treatment. Equipment and technology have only recently allowed epidurography to diagnose and treat these most difficult and incapacitating medical conditions. Because the epidural space is continuous with the dura and the neuro-foramina, it is the obvious starting cavity to diagnose and treat many of the epidural afflictions.

Therefore, there is still a need for a device for and a method of epidural exploration and surgery that allows a physician or use to effectively enter the epidural space, visually observe a problem area, and therapeutically treat the problem area in or around the epidural space in a minimal amount of time and with minimal amount of damage.

SUMMARY OF THE INVENTION

The present invention provides devices for and methods of treating afflictions occurring in a body cavity, such as the epidural space. The methods and devices provide for fluoroscopic assisted placement of a fiber optic catheter/scope with a balloon tip. These devices and methods would perform decompression surgery, neuroplasty, and mechanical lysis of adhesions (and other afflictions), as well as allowing small operating and therapeutic instruments under direct visualization.

BRIEF DESCRIPTION OF THE DRAWINGS

FIGS. 1-4, 5a-5b, 6a-6b, 7a-7e, 8, and 9a-9b are views of medical devices and methods of using the same according to the present invention. FIGS. 4, 5a-5b, 6a-6b, 7a-7e, 8, and 9a-9b presented in conjunction with this description are views of only particular—rather than complete—portions of the medical devices and methods of using the same.

DETAILED DESCRIPTION OF THE INVENTION

The following description provides specific details in order to provide a thorough understanding of the present invention. The skilled artisan, however, would understand that the present invention can be practiced without employing these specific details. Indeed, the present invention can be practiced by modifying the illustrated structural member and method and can be used in conjunction with apparatus and techniques conventionally used in the industry. For example, the devices and methods are described with reference to the epidural space and the afflictions associated therewith. The devices and methods of the present invention, however, could easily be adapted for other body cavities and their associated afflictions.

The devices of the present invention are able to perform at least three functions simultaneously. First, the devices of the present invention are steerable. Second, the devices of the present invention are optical. Finally, the devices of the present invention are inflatable. By exhibiting these three functions simultaneously, the devices (and methods) of the present invention are more effective and easier to use than known devices.

The devices of the present invention are made steerable using any suitable means known in the art. Suitable means include any mechanism that allows a user of the device to control the direction of the device. Examples of suitable steerable means include those described in U.S. Pat. Nos. 5,857,996 and 5,399,164, the disclosures of which are incorporated herein by reference.

The devices of the present invention are made optical using any suitable means known in the art. Suitable means include any mechanism that allows a user of the device to view the proximity of the body cavity near the device. Examples of suitable optical means include those described in U.S. Pat. Nos. 5,857,996, 4,961,738, 5,399,164, and 5,215,105, the disclosures of which are incorporated herein by reference.

The devices of the present invention are made inflatable using any suitable means known in the art. Suitable means include any mechanism that allows a user of the device to expand a portion of the device when desired. Examples of suitable inflatable means include balloons and the like, as well as those means described in U.S. Pat. Nos. 4,961,738, and 4,519,403, 5,084,016, and 5,215,105, the disclosures of which are incorporated herein by reference.

Besides the above three functions, the devices can contain any other features known in the art which aid the devices to serve additional functions. As well, the devices of the present invention can have any configuration that provides the above three features. A preferred configuration for the devices of the present invention for achieving the above three functions is illustrated in the Figures.

Figure 1:
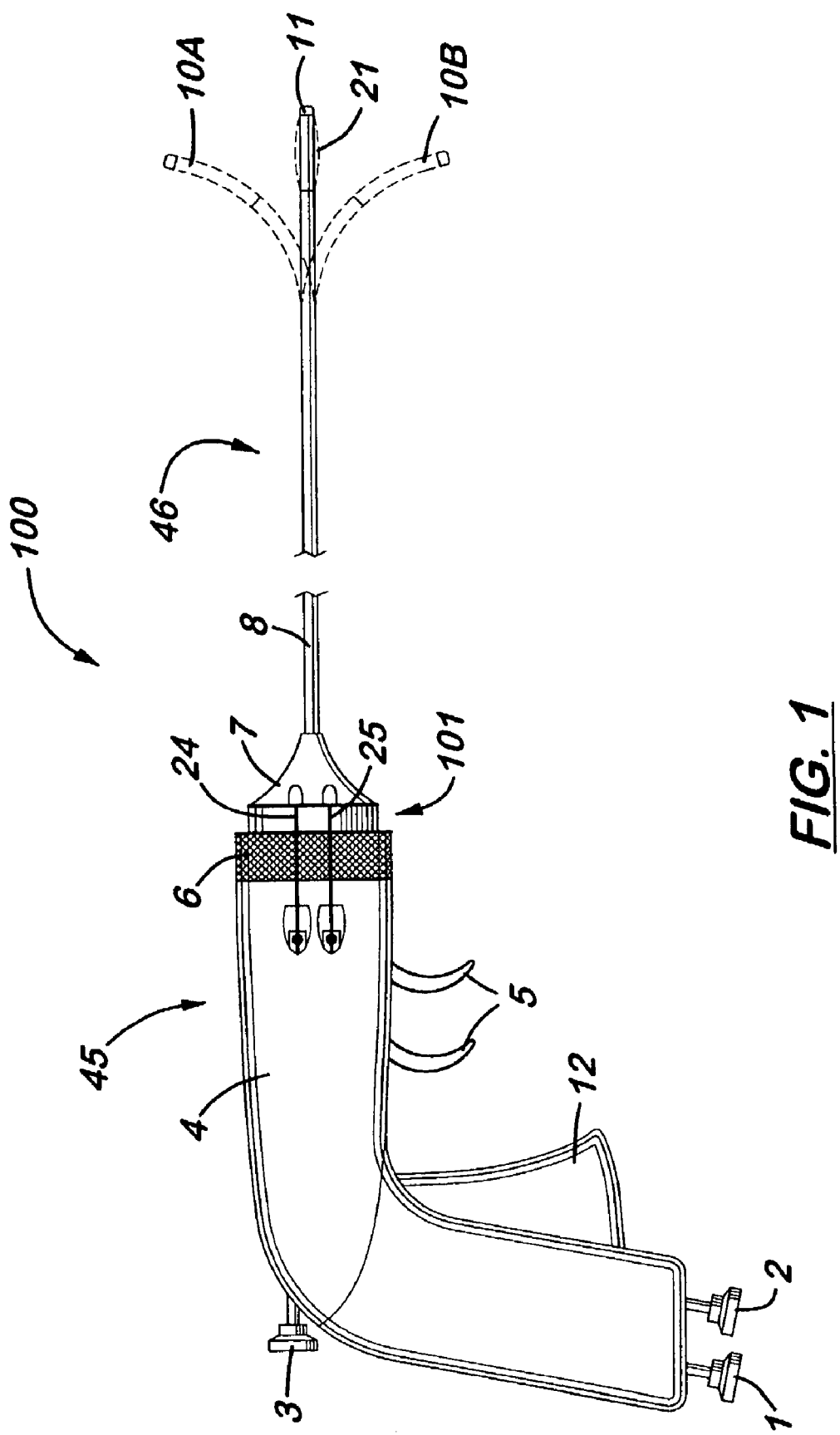

In the aspect of the present invention illustrated in the Figures, device 100 comprises three main portions: a disposable catheter portion, a reusable handling portion, and a connecting portion. The reusable handling portion allows an operator to hold—either by hand or by using a mechanical apparatus—device 100 and to control the device. Thus, any suitable mechanism which serves such functions can be employed in the present invention. See, for example, U.S. Pat. Nos. 5,857,996 and 5,399,164, the disclosures of which are incorporated herein by reference. Preferably, the handling portion 45 illustrated in FIG. 1 is employed in the present invention. In one aspect of the invention, the handling portion can be made disposable instead of reusable.

The disposable catheter portion allows an operator to access, analyze, and treat the desired body cavity, such as the epidural space. Thus, any suitable mechanism which serves such a function can be employed in the present invention. See, for example, U.S. Pat. Nos. 5,857,996, 5,215,105, 4,519,403, and 4,961,738, the disclosures of which are incorporated herein by reference. Preferably, the catheter portion 46 illustrated in FIG. 1 is employed in the present invention.

The handling portion and the disposable catheter portion are connected using a connecting portion, e.g., suitable connection means known in the art. Suitable connection means are those devices or apparatus which removably connect these two portions, yet (as described below) allow communication between these portions. Preferably, the connection portion 101 illustrated in FIG. 1 is employed in the present invention. The connecting portion can be part of or separate from either the handling portion or the catheter portion.

The material for the handling portion, catheter portion, and connection portion (unless specified otherwise) can be made of any suitable medical grade material. Examples of suitable medical grade materials include polymeric materials, plastic materials, rubber materials, elastomeric materials, silastic, silicone, and PVC. Preferably, polyurethane is used in the present invention as this material.

In the aspect of the present invention is illustrated in the Figures, body 45 (handling portion) is connected to catheter 46 (catheter portion) by locking collar 6 and proximal collar 7 (collectively, the connecting portion). Body 45 comprises housing 4 which contains at least one control means and at least one communication means. The control means allow a user to actuate and control the various functions of device 100, including the three functions described above. Thus, any suitable control means known in the art can be employed in the present invention. The conveyance means allows the handling portion to convey the instructions from the control means in the handling portion to the catheter portion. Thus, any suitable conveyance means known in the art can be employed in the present invention.

In one aspect of the invention, a single control means and a single conveyance means can be employed for all the functions desired of device 100. In a preferred aspect of the invention, however, multiple control means and multiple conveyance means are used, with each control means and conveyance means controlling a single function. Thus, for example, a first control means and a first conveyance means could be used for the inflatable function, a second control means and a second conveyance means could be used for the visualization (fluoroscopic) function, etc. . . ..

For example, a first control means and a first conveyance means are employed to aid in the inflatable function of device 100. In FIG. 7*a*, trigger 12 is hinged at 49 and is connected to a pump plunger 47 and a pump 34. Pump 34 can pump any suitable fluid 9, e.g., a liquid such as saline solutions, water, contrast agents, pharmaceuticals, or anesthetics; a gas such as air; a gas containing a solid such as a suspension; a liquid containing a solid such as a slurry; or a gas containing a liquid. The fluid 9 is pumped from a reservoir (not shown) that is either internal or external to body 45. Pump 34 pumps the selected fluid 9 through tube 35 and into catheter 46. Tube 35 is made of any suitable material which will handle the selected fluid, such as plastic. Tube 35 is provided with fitting 48 that will connect tube 35 to pump 34. Tube 35 is connected at the other end to manifold 51. Since manifold 51 is attached to housing 4, manifold 51 serves to anchor tube 35 to housing 4. By actuating trigger 12, a user is able to pump fluid 9 from the reservoir, through tube 35, through manifold 51, and to the catheter portion. Fluid 9 will be used, as described below, to inflate the inflatable means of device 100.

In a similar manner, additional control means and conveyance means can be provided for the additional functions desired of device 100 as shown in FIG. 7*b*. Tube 36 can also be provided for the optical function of device 100. Tube 36 is provided in housing 4 and is connected at one end to manifold 51 and at the other end to viewing port 2, which in one aspect of the invention is a video connection port. Tube 37 can also be provided for the optical function of device 100. Tube 37 is connected at one end to manifold 51 and, at the other end to light source port 1, which in one aspect of the invention is a light injection port. These tubes, along with their associated ports, aid a user to use device 100 to view the body cavity under inspection.

Other control and conveyance means can be used for the steering function of device 100 as shown in FIG. 7*a*. Two triggers 5 are connected to spring loaded chamber 39 that is connected to housing 4. Spring loaded chamber 39 is connected to attachment rod 40 that has an attachment point 102 to allow connection of a first deflection wire 24 and a second deflection wire 25. The first and second deflection wires are not connected to manifold 51, but instead pass through manifold 51 via ports 27. As described below, these elements of device 100 are used to aid a user in steering device 100.

As shown in FIG. 7*b*, Tube 38 can be provided for additional functions, such as introducing other instruments or injecting other fluids. Tube 38 is connected at one end to manifold 51 and, at the other end, to port 3, which in one aspect of the invention can serve to introduce fluids, gas, or micro surgical/therapy instruments. If desired, additional control and conveyance means can be provided for additional functions for device 100.

As illustrated in FIG. 1, body 45 contains manifold 51, which secures the conveyance means within handling portion. The control means of the handling portion are already affixed thereto, so there is no need to secure them The conveyance means (tubes and wires), however, are attached to the control means at one end and therefore need to be secured to manifold 51 at their other end. Manifold 51 is also connected to tubes 35, 36, 37, 38 (and others, if desired) so as to allow materials associated with that respective tube to pass through manifold 51 and into the catheter portion. Any suitable connection which allows such a transfer can be employed in the present invention. One suitable connection is indexing ports 41, 42, 43, 50 as illustrated in FIGS. 7*c* and 7*d* that are respectively associated with tubes 35, 36, 37, and 38, and serve as an "end" to the tubes, and allow the materials to pass through manifold 51.

As shown in the Figures, connection portion between handling portion and disposable catheter portion comprises several elements besides the connection means which aid in the operation of the device. Connection portion comprises locking collar 6 and proximal collar 7. These two collars serve to removably connect handling portion and catheter portion using any suitable mechanism known in the art. For example, proximal collar 7 which has previously been attached to catheter 46—can be screwed onto body 45 using locking collar 6 and threads 52, thereby removably connecting the handling portion with the catheter portion as shown in FIGS. 7*a* and 7*b*. In this process of connection, manifold 51 that is located in body 45 abuts to manifold 30 that is located in proximal collar 7 as shown in FIG. 6*a*.

As depicted in the Figures, proximal collar 7 contains manifold 30 which serves a similar function as manifold 51. Manifold 30 also contains indexing ports 31, 32, 33, and 53 that serve the same functions as the indexing ports 41, 42, 43, and 50, but are merely located in manifold 30 instead of manifold 51. When attached to locking collar 6 (which is connected to body 45), manifold 30 abuts manifold 51 with the indexing ports of manifold 30 matched with the corresponding indexing ports of manifold 51.

As illustrated in the Figures, the combination of the two sets of indexing ports allows materials in the tubes located in the handling portion to pass into the catheter portion. The fluids and light from tubes 35, 36, 37, and 38 pass through the indexing ports in manifold 51, through the index ports of manifold 30, and to the catheter portion. Manifold 30 is connected to tubes 54, 55, 56, 57 as described below. Thus, the materials associated with that respective tube to pass through manifold 51, through manifold 30, and into matching tubes in the catheter portion.

Figure 8:
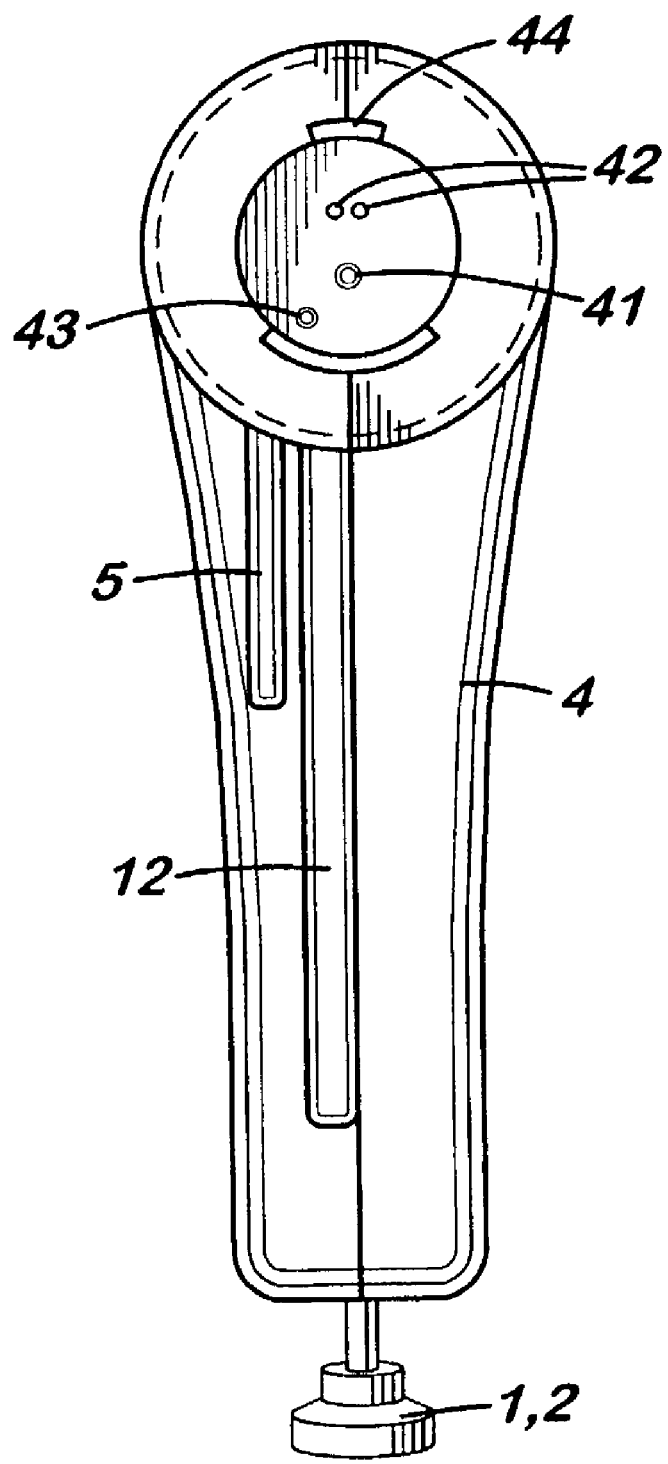
Figure 9A:
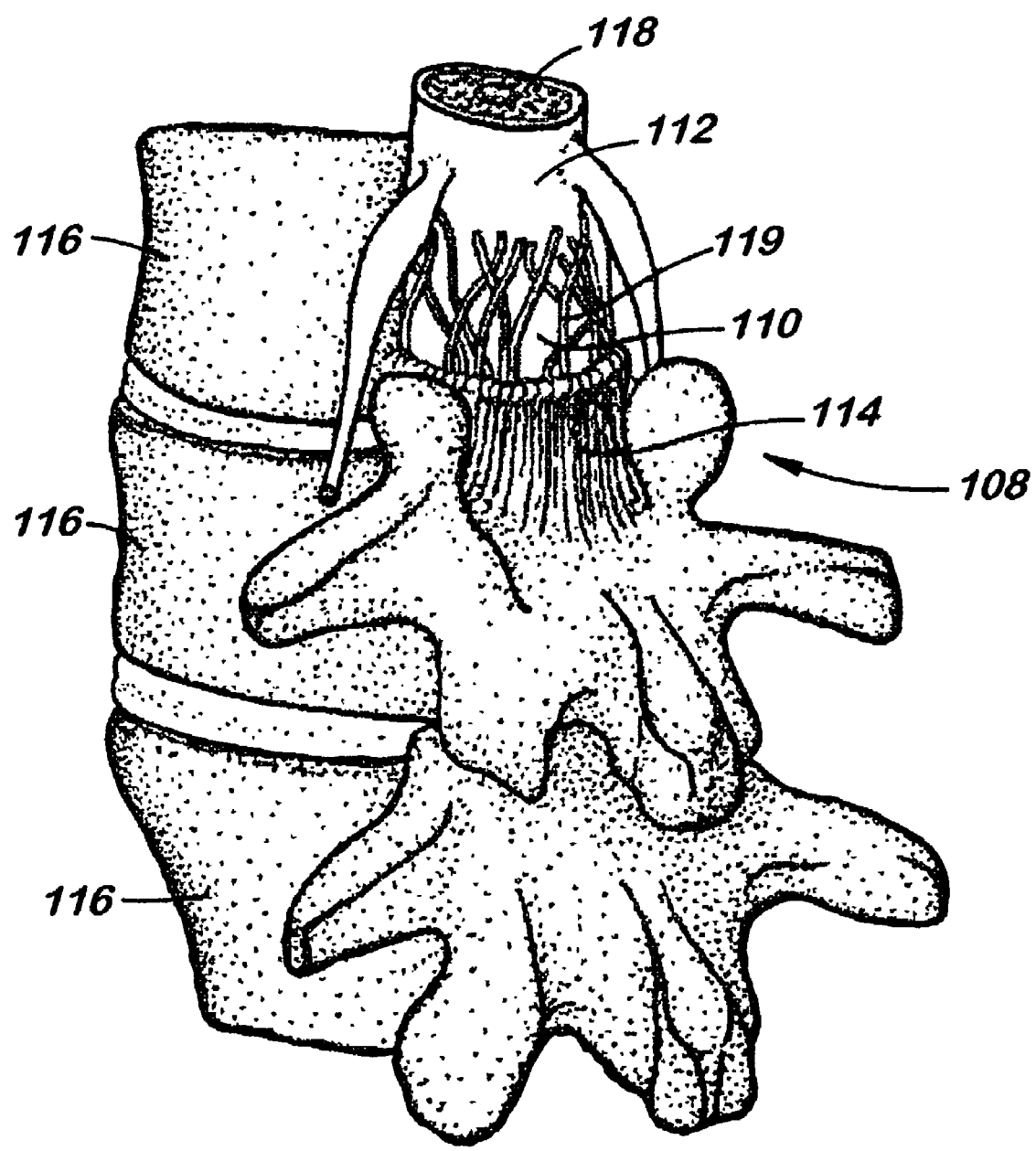
Figure 9B:
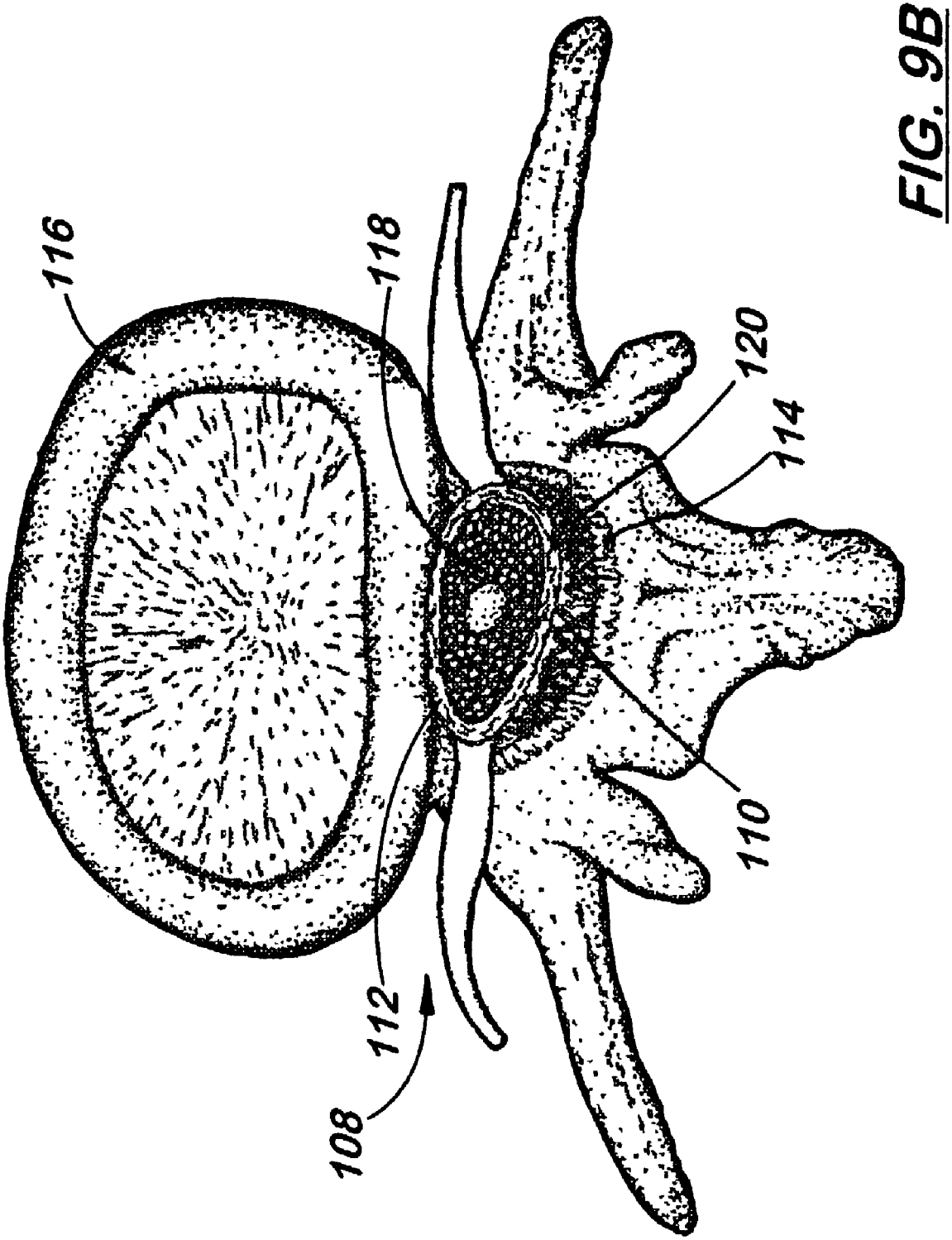

As shown in FIG. 8, connecting portion contains means for aligning the handling portion and the catheter portion. One suitable aligning means is indexing lug 44, which makes sure catheter portion is aligned properly with the handling portion. Indexing lug 44 also makes sure that manifold 51 is aligned properly with manifold 30. Indexing lug provides the alignment by indexing with slot 28 in a proximal collar 7 as shown in FIGS. 5*a* and 6*a*.

If necessary, sealing means-such as gaskets-an be provided in device 100 where necessary. For example, as shown in FIGS. 5*a* and 6*a*, manifold 30 is provided with gasket 29 that seals a injection index port 33 from leaking when fluids or materials are passed through it. In another example, gasket 154 can be provided for port 53 from leaking when fluids or materials are passed through it. Additional gaskets for the other indexing ports, and other parts of device 100, can be added where necessary.

As shown in FIGS. 5*b* and 6*b*, catheter portion comprises catheter shaft 8 which contains at least one conveyance means. The conveyance means allows the catheter portion to convey the materials from the handling portion through manifold 30 to the respective location of the catheter portion where these materials perform the desired operation. Thus, any suitable conveyance means known in the art can be employed in the present invention. In one aspect of the invention, tubes 54, 55, 56, 57 are employed as the conveyance means in the catheter portion (similar to tubes 35, 36, 37, 38 used as the conveyance means in the handling portion and depicted in FIGS. 7a and 7b).

As illustrated in FIGS. 6a and 6b, manifold 30 is connected to tubes 54, 55, 56, and 57 with any suitable connection means known in the art. Any suitable connection which allows such a transfer can be employed in the present invention. One suitable connection means are indexing ports 31, 32, 33, and 53 as illustrated in FIG. 6a that are respectively associated with tubes 54, 55, 56, and 57, and serve as an "end" to the tubes and allow the materials to pass through manifold 30.

Figure 2:
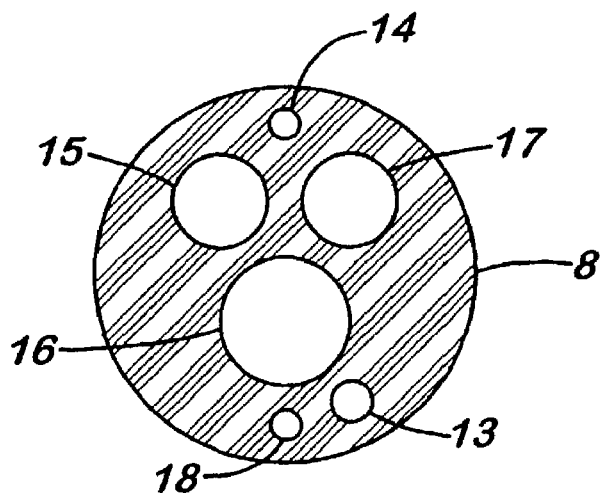

Like the tubes in the handling portion, the tubes in the catheter portion aid device 100 in carrying out the specified functions. For example, as depicted in FIG. 2, tube 55 is associated with a video port 17 in catheter shaft 8. Tube 56 is associated with a light injection port 15 in catheter shaft 8. Tube 54 is associated with balloon injection port 13 in catheter shaft 8. Tube 57 is associated with injection/instrument port 16 in catheter shaft 8.

Catheter shaft 8 is connected to proximal collar 7 using any suitable means known in the art that will allow these two components to remain in a fixed orientation or alignment. By fixing the alignment between these two components, two holes 27 can be placed a proximal collar 7 that will allow first deflection wire 24 and second deflection wire 25 to exit from proximal collar 7 and be connected to attachment rod 40 in body 45 when the handling portion is connected to the catheter portion.

Figure 3:
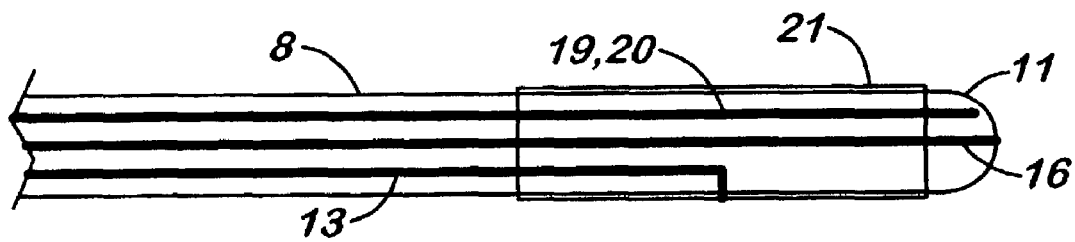

As depicted in FIG. 3, catheter shaft 8 extends about a central axis to distal end 11. Shaft 8 may be formed from a material-such as a semi-soft polymer like a polyester elastomer—which provides good columnar strength and collapse resistivity while allowing some flexibility. The end 11 of a catheter shaft 8 is a soft clear tip made of any suitable material. Suitable materials include those which will not damage or otherwise adversely impact sensitive and delicate internal structures. Suitable materials include any of the medical grade materials described above. The catheter shaft 8 can be made to fit any desired length or diameter. Optionally, the tip of catheter shaft can be tapered (as known in the art) to facilitate penetration of tissues during insertion into the body cavity.

Figure 4:
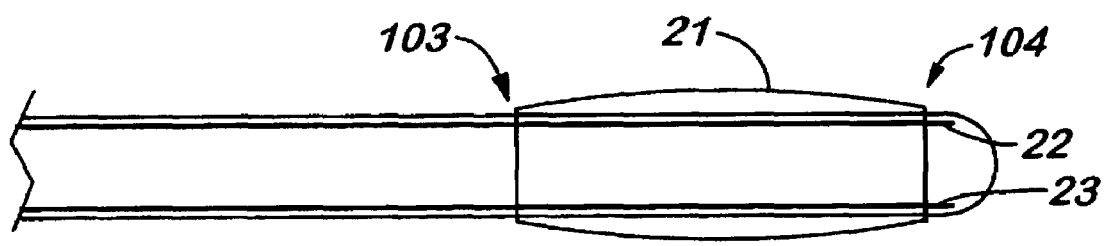

As illustrated in FIG. 4, first deflection wire 24 and second deflection wire 25 run the length of flexible catheter shaft 8 through ports 14 and 18. These deflection wires are anchored in the soft tip of catheter shaft 8 at positions 22 and 23. These deflection wires can be made of any suitable material, such as stainless steel, and configured so they are strong, yet flexible. When these wires are contracted, they "pull" flexible shaft into positions 10a and 10b, as shown in FIG. 1, because they are anchored to the tip. The tip can be "pulled" by any either wire at an angle (relative to the axis of shaft 8) ranging from 0 degrees to about 180 degrees. Thus, the tip can encompass a full 360 degree range of motion.

Catheter shaft 8 also contains balloon injection port 13, as illustrated in FIG. 3. This port runs the length of the shaft and terminates at the flexible balloon 21 near the end of catheter shaft 8. This port also encloses and contains tube 54. As fluid 9 is pumped from the handling portion, it enters through port 13 and travels the length of tube 54 and enters flexible balloon 21. Balloon 21 inflates as additional amounts of fluid 9 are pumped into it.

Balloon 21 is attached to catheter shaft 8 at the ends of the balloon at locations 103 and 104. Thus, when fluid 9 enters the cavity created by balloon, the ends remain attached to the shaft while the middle inflates. The ends of balloon 21 can be attached to the catheter shaft by any suitable mechanisms or method known in the art, such as by thread winding and a bonding agent. In one aspect of the invention, the ends of the balloon are attached by RF welding. Balloon 21 can be made of any suitable material known in the art, such a s compliant material like latex or silicone rubber.

Balloon 21 is preferably a low pressure, high-volume balloon. The inflated outer diameter of the balloon is dependent upon the space in which the balloon is inflated. Once the balloon reaches a maximum radial dilation, it expands longitudinally within the epidural space. In this manner, the expansion of the balloon is adequate to rupture the fibrosis of the epidural lesion while preventing damage within the nerves within the cavity such as the epidural space or damage to the dura mater and the spinal column itself. The maximum pressure at which the balloon may be inflated is about 250 mm Hg. Balloon inflation time preferably should not exceed 10 seconds, while balloon deflation time should not exceed 30 seconds. The volume of balloon 21 when inflated is preferably less than 1 cc.

Tubes 56, 57, and 55 run the length of catheter shaft respectively through ports 15, 16, and 17. Ports 15, 16, and 17 are open at their respective ends. The light 19 (for illuminating) enters through tube 56, travels along port 15, and then exits into the body cavity. The light 20 (for viewing) is then reflected from the body cavity, travels along port 17, and back through tube 55. Instruments or other fluid injections are inserted through tube 57, along port 16, and exit into the body cavity.

Device 100 operates in the following manner. The device is steered by using triggers 5. The force applied to a trigger by a user will pull the desired attachment rod which will, in turn, pull on the appropriate wire. The action of pulling the wire will cause the distal end 11 of the catheter shaft 8 to deviate from the distal end at the desired angle from the shaft axis. Releasing the trigger will then return the distal end 11 to its position along the shaft axis.

In one aspect of the invention, additional wires (with the accompanying elements such as ports in the manifolds, triggers, etc . . . ) can be added for additional directions and dimensions of tip deviation. In another aspect of the invention, the mechanical means for tip deviation (the wires and associated elements) can be replaced with non-mechanical (i.e., magnetic or electromagnetic) means for tip deviation.

A user can view the body cavity using device 100 in the following manner. Although device 100 is described using fiberoptics, any fluoroscopic means could be employed. A light source is attached to port 1 to send light along tube 37. The light passes through manifold 51 via port 43, through manifold 30 via port 33, into tube 56 along port 15, and then exits into the body cavity. The light 20 (for viewing) is then reflected from the body cavity, travels along port 17, and back through tube 55, through manifold 30 via port 32, through manifold 51 via port 42, through tube 36, and through video connection port 2 where the image is displayed in any desired display medium.

A user inflates the inflatable means (balloon) of device 100 in the following manner. Actuating trigger 12 will cause pump 34 to pump fluid 9 from the reservoir and inject the fluid along tube 35, through manifold 51 via port 41, through manifold 30 via port 31, through tube 54 in port 13, and into balloon 21. The more fluid 9 that is injected, the more the balloon is inflated. Once the balloon is inflated to the desired level, the trigger 12 is slowly released. The negative pressure caused by the release will cause fluid 9 to reverse direction along this path and return to the reservoir.

Instruments or other injections are inserted through port 3, along tube 38, through manifold 51 via port 50 through manifold 30 via port 53, through tube 57 in port 16, and into the body cavity. These instruments can be used for various surgical procedures as known in the art. Other liquids, such as steroic liquids for treatment or radioactive liquids for fluoroscopic analysis, can also be injected in a similar manner.

Generally, by using device 100 a user can control and manipulate the catheter 46 while simultaneously viewing the body cavity under inspection. Further, a user can positionally locate, isolate, and view problem, as well as visually record and visually document the problem area. Since catheter 46 is flexible and maneuverable within the epidural space, the method also provides less radical interspinal surgical operations because problem areas can more effectively be observed and accessed with the optical and steerable combined functions. The device of the present invention can be used for any type of surgery known in the art, including laser, ultrasound, and electrocautery surgeries.

Specifically, the devices of the present invention are used to treat afflictions within any cavity of the body. In one aspect of the invention, the devices of the present invention are employed in methods for treating fibrotic lesions in the epidural space of the spinal column. One such method involves inserting a device of the present invention into the epidural space using the steerable and fiberoptic functions of the device. Once located in the epidural space, the fiberoptic and steerable mechanisms of the device are used to quickly and efficiently explore and analyze the epidural space. Once an affliction is located in the epidural space—such as a fibrotic lesion, adhesion, or scar tissue—the inflatable mechanism is used to dilate the epidural space, decompress adhesions, and remove scar tissue. When a balloon is used as the inflatable mechanism, the balloon is positioned across the fibrotic lesion, and the balloon is inflated radially and/or longitudinally to sever or disrupt the fibrosis comprising the epidural lesion.

To perform a treatment, as known in the art, a needle is first used to access the sacral foramen. The ligamentumflavum, 24 is then pierced and the needle tip is inserted in the sacral hiatus or other spinal levels. A guide wire is inserted and advanced through the needle and into the epidural space. The needle is extracted from the epidural space 110 and discarded. A dialating or introducer sheath can then be placed over the guide wire.

The catheter 46 is then inserted through the introducer sheath over the guide wire and into the opening to the epidural space 110. The guide wire functions to guide catheter 46 into the sacral hiatus. Because the catheter 46 is a steerable catheter, the body 45 and flexible distal end 11 ease the advancement and positioning of the catheter within and around the epidural space. If desired, the position of the steerable catheter within the epidural space may also be fluoroscopically observed as known in the art. Once in the epidural space, device 100 is advanced into the distended portion of the epidural space. The optical function of device 100 illuminates the distended portion of the epidural space to thereby visualize and display the epidural space and a problem area therein. The problem area is then analyzed. The catheter can be manipulated to place the distal end 11 into an optimal position, e.g., one where balloon 21 could be inflated but without hindering positioning of instruments or devices used in surgical procedures.

Then, the requisite treatment is performed using the balloon or other instruments/injections to disrupt a fibrotic lesion, performing a diskectomy, or other types of procedures. In one aspect of the invention, fluid 9 is used to inflate balloon 21. As balloon 21 inflates, it expands radially outwardly, concentrically about shaft 8, rupturing and dislodging the fibrosis as it expands. As inflation of the balloon 21 continues, the outer diameter of the balloon expands toward the walls of the epidural space compressing the fibrosis therebetween, exerting a force against the walls of the epidural space. As inflation continues further, the pressurized fluid in the balloon 21 interior finds the path of least resistance, causing the balloon to expand longitudinally within the epidural space and parallel to the axis of shaft 8.

As balloon 21 expands longitudinally, the force against the walls of the epidural space is maintained. In this manner, the longitudinal expansion of balloon 21 further increases the surface area of the balloon which contacts, ruptures and compresses the fibrosis of the lesion. As known in the art, the size and shape of the epidural space will affect the extent of radial and longitudinal expansion of balloon 21. After balloon 21 has been inflated and the fibrosis treated, negative pressure is applied to the interior of the balloon as described above, causing deflation of the balloon. The catheter 46 then may be repositioned to treat an adjacent portion of the same lesion or to treat another lesion at a different site. After the dilatation(s) and any other desired medical procedures have been completed, the catheter is withdrawn from the epidural space.

The method of the present invention thereby provides improved visualization of the epidural space and more effective treatment of problems areas therein. The method allows the user to effectively observe and document the problem area and then determine the most effective treatment for the patient. Since the steerable catheter is preferably quite flexible and maneuverable within the epidural space, the method also provides less radical interspinal surgical operations because problem areas can more effectively be observed and accessed with the optical and steerable combination.

Having described the preferred embodiments of the present invention, it is understood that the invention defined by the appended claims is not to be limited by the particular details set forth in the above description, as many apparent variations thereof are possible without departing from the spirit or scope thereof.

I claim:

1. A medical device for treating disorders within an epidural space, comprising:
   a body;
   a catheter portion connected to said body at a proximal end and extending from said body to a distal end;
   an inflatable member disposed on an exterior surface of said catheter portion and spaced away from said distal end, such that said distal end of said catheter extends beyond said inflatable member so as to penetrate patient tissue ahead of said inflatable member during use; and
   a steering mechanism integrated into said catheter portion, wherein the catheter portion is flexible and the steering mechanism controls an angle of the distal end with respect to an adjacent segment of said catheter portion such that said distal end and said inflatable member can be steered without, or after being advanced beyond an end of, a guidewire;
   an optical system, connected to said body, configured to obtain an image of said epidural space around said distal end of said catheter and provide that image to an operator of said medical device;
   wherein said medical device is specifically configured for treating disorders within an epidural space with minimal damage to a patient.

2. The device of claim 1, wherein the inflatable member comprises at least one balloon.

3. The device of claim 1, wherein said optical system comprises fiber optics extending through said catheter portion to said distal end.

4. The device of claim 1, further comprising a reservoir in said body from which said inflatable member is inflated using controls on said body.

5. The medical device of claim 4, wherein said body is shaped like a gun and said balloon is inflated by actuating a trigger at a handle portion of said body.

6. The device of claim 1, further comprising a tube running through said catheter portion for delivering an instrument or fluid to said distal end of said catheter portion.

7. The medical device of claim 1, wherein said body has an L-shape.

8. The medical device of claim 1, wherein said steering mechanism comprises wires extending through said catheter portion to said distal end.

9. The medical device of claim 1, wherein said inflatable member extends along a length of said catheter portion away from said distal end.

10. The medical device of claim 1, wherein said both forward and rearward ends of said inflatable member are attached to said catheter portion such that, when inflated, a middle portion of said inflatable member experiences the most expansion.

11. The medical device of claim 10, wherein when said middle portion of said inflatable member reaches a maximum radial expansion, the inflatable member then expands longitudinally.

12. A method of operating a medical device to treat an epidural space of a patient, wherein said medical device includes
a body,
a catheter portion extending from said body and having a distal end,
an optical system, connected to said body, configured to obtain an image of said epidural space around said distal end of said catheter and provide that image to an operator of said medical device;
a steering mechanism integrated into said catheter portion, and
an inflatable member disposed along said catheter portion and spaced away from said distal end,
said method comprising:
inserting said distal end of said catheter into said epidural space of said patient;
obtaining an image of said epidural space with said optical system to locate an area of said epidural space to be treated;
penetrating tissue in said epidural space with said distal end of said catheter portion by applying force to said body of said device;
then inflating said inflatable member disposed along said catheter portion behind said distal end in tissue already penetrated by said distal end to apply pressure to the penetrated tissue, and
steering the catheter portion with the steering mechanism inside said epidural space to locate said tissue that is penetrated with said distal end, wherein the catheter portion is flexible and the steering mechanism controls an angle of the distal end with respect to an adjacent segment of said catheter portion such that said distal end and said inflatable member can be steered without, or after being advanced beyond an end of, a guidewire.

13. The method of claim 12, wherein said tissue penetrated comprises a lesion in said epidural space.

14. The method of claim 12, further comprising providing fluid or an instrument to said distal end through a tube in said catheter portion.

15. The method of claim 12, further comprising rupturing said penetrated tissue with inflation of said inflatable member.

16. The catheter of claim 12, wherein said steering mechanism comprises a plurality of wires for steering said shaft by controlling an orientation of said tip.

17. The method of claim 12, further comprising inflating said inflatable member to less than 250 mm Hg to avoid damage to nerves or dura in said epidural space.

18. The method of claim 12, further comprising rupturing fibrosis of an epidural lesion with inflation of said inflatable member.

19. The method of claim 12, further comprising dilating the epidural space with inflation of said inflatable member.

20. The method of claim 12, further comprising removing scar tissue from the epidural space with inflation of said inflatable member.

21. The method of claim 12, wherein said penetrating tissue in said epidural space with said distal end of said catheter portion further comprising penetrating said tissue by applying force to said body by band of an operator of said device.

22. A medical device comprising:
a body comprising a locking collar;
a shaft connected to said body by said locking collar at a proximal end of said shaft and extending from said body to a tapered distal end that is configured to penetrate tissue to be treated, said distal end penetrating the tissue due to force applied by hand to said body by an operator of said device;
an inflatable member disposed on an exterior surface of said shaft and spaced away from said distal end, such that said tapered distal end of said shaft extends beyond said inflatable member so as to penetrate patient tissue ahead of said inflatable member during use, said shaft further comprising a fluid pathway for inflating said inflatable member by introducing fluid into said proximal end of said shaft at said body and delivering that fluid to said inflatable member, wherein the fluid is drawn from a closed reservoir disposed inside said body and having a specific, limited amount of fluid therein such that inflation of the inflatable member can be limited so as not to exceed a predetermined amount or pressure, said body further comprising a pump for moving fluid from said reservoir in said body to said inflatable member through a manifold anchored to said body and from said manifold into said fluid pathway;
a steering mechanism integrated into the shaft and controlled by controls on said body, wherein the distal end of said shaft is flexible and the steering mechanism controls an angle of the distal end with respect to an adjacent segment of the shaft such that said distal end and the inflatable member can be steered without, or after being advanced beyond an end of, a guidewire, said steering mechanism comprising wires passing trough ports in said manifold and extending along said shaft;
an optical system comprising at least one pathway integrated into the shaft through which illumination can be provided to said distal tip of said shaft and through which images can be obtained of an environment at the distal end of the shaft, said at least one optical pathway being connected to said manifold; and
a catheter integrated into the shaft through which either a tool or fluid can be introduced at the body and delivered at said distal end of the shaft,
wherein said device is specifically configured for use in an epidural space.

* * * * *

UNITED STATES PATENT AND TRADEMARK OFFICE
CERTIFICATE OF CORRECTION

PATENT NO. : 7,273,468 B2
APPLICATION NO. : 10/169641
DATED : September 25, 2007
INVENTOR(S) : Raymond L. Bedell It is certified that error appears in the above-identified patent and that said Letters Patent is hereby corrected as shown below:

Column 12, Line 18, Claim 21, change "by applying force to said body by band" to --by applying force to said body by hand--

Column 12, Line 53, Claim 22, change "trough ports in said manifold and extending" to --through ports in said manifold and extending--

Signed and Sealed this

Twenty-sixth Day of February, 2008

JON W. DUDAS
*Director of the United States Patent and Trademark Office*